United States Patent
Green et al.

(10) Patent No.: US 9,931,441 B2
(45) Date of Patent: Apr. 3, 2018

(54) SPECIALLY DESIGNED MAGNESIUM-ALUMINUM ALLOYS AND MEDICAL USES THEREOF IN A HEMODYNAMIC ENVIRONMENT

(71) Applicant: Transluminal Technologies, LLC, Syracuse, NY (US)

(72) Inventors: Stephen Green, Syracuse, NY (US); Rudolph Buchheit, Columbus, OH (US)

(73) Assignee: TRANSLUMINAL TECHNOLOGIES, LLC, Syracuse, NY (US)

( * ) Notice: Subject to any disclaimer, the term of this patent is extended or adjusted under 35 U.S.C. 154(b) by 0 days.

(21) Appl. No.: 14/879,275

(22) Filed: Oct. 9, 2015

(65) Prior Publication Data
US 2017/0128630 A1    May 11, 2017

Related U.S. Application Data (62) Division of application No. 13/292,960, filed on Nov. 9, 2011, now Pat. No. 9,155,530.

(60) Provisional application No. 61/411,698, filed on Nov. 9, 2010.

(51) Int. Cl.
| | |
|---|---|
| A61F 2/06 | (2013.01) |
| A61L 31/02 | (2006.01) |
| A61B 17/00 | (2006.01) |
| A61L 27/04 | (2006.01) |

(52) U.S. Cl.
CPC ........ *A61L 31/022* (2013.01); *A61B 17/0057* (2013.01); *A61L 27/047* (2013.01); *A61B 2017/00831* (2013.01)

(58) Field of Classification Search
CPC ...... A61B 17/0057; A61B 2017/00831; A61B 17/00; A61B 17/08; A61F 2/06
See application file for complete search history.

(56) References Cited

U.S. PATENT DOCUMENTS

| | | | |
|---|---|---|---|
| 3,099,083 A * | 7/1963 | De Long | C23F 13/02 29/428 |
| 6,042,601 A | 3/2000 | Smith | |
| 2005/0085856 A1 | 4/2005 | Ginn | |

(Continued)

FOREIGN PATENT DOCUMENTS

| | | |
|---|---|---|
| EP | 1440661 | 7/2004 |
| WO | 9922646 | 5/1999 |

(Continued)

OTHER PUBLICATIONS

Memo Concerning the Official Action Reported in Mexican Patent Appln. No. MX/a/2013/005265 dated Apr. 6, 2017, 2 pages.

(Continued)

*Primary Examiner* — Victor Nguyen
(74) *Attorney, Agent, or Firm* — Bond Schoeneck & King, PLLC; George McGuire; Frederick Price

(57) ABSTRACT

The present invention relates generally to specially designed magnesium-aluminum ("Mg—Al") alloys and medical uses thereof in a hemodynamic environment, and, more particularly to devices for sealing an opening formed through biological tissue (such as blood vessels) made from such specially designed magnesium-aluminum alloys.

19 Claims, 10 Drawing Sheets

(56) References Cited

U.S. PATENT DOCUMENTS

| | | | |
|---|---|---|---|
| 2006/0052825 A1 | 3/2006 | Ransick et al. | |
| 2007/0021770 A1 | 1/2007 | Brenneman et al. | |
| 2009/0069844 A1* | 3/2009 | Green | A61B 17/0057 606/213 |

FOREIGN PATENT DOCUMENTS

| | | |
|---|---|---|
| WO | 2009035921 | 3/2009 |
| WO | 2012/061486 | 5/2012 |
| WO | 2012064888 | 5/2012 |

OTHER PUBLICATIONS

EP Supplementary European Search Report dated Oct. 31, 2014, pp. 1-7.
EP Supplementary European Search Report dated Sep. 7, 2015, pp. 1-6.
EP Supplementary European Search Report dated Nov. 17, 2015, pp. 1-8.
Spruson & Ferguson Intellectual Property Examination Report dated Dec. 1, 2015, pp. 1-7.

* cited by examiner

SPECIMEN, PRE-IMPLANTATION

FIG. 4

ANTERIOR EXPOSURE, POST IMPLANTATION

FIG. 5

FIG. 6C
RIGHT FEMORAL, 4 hrs

FIG. 6D
RIGHT FEMORAL, 8 hrs

FIG. 6A
LEFT FEMORAL, 4 hrs

FIG. 6B
LEFT FEMORAL, 8 hrs

SPECIALLY DESIGNED MAGNESIUM-ALUMINUM ALLOYS AND MEDICAL USES THEREOF IN A HEMODYNAMIC ENVIRONMENT

RELATED APPLICATION DATA

The present application is a divisional of co-pending U.S. patent application Ser. No. 13/292,960, filed on Nov. 9, 2011, which claims benefit of U.S. provisional patent application No. 61/411,698, filed on Nov. 9, 2010; all of the foregoing patent-related document(s) are hereby incorporated by reference herein in their respective entireties.

BACKGROUND OF THE INVENTION

1. Field of Invention

The present invention relates generally to specially designed magnesium-aluminum ("Mg—Al") alloys and medical uses thereof in a hemodynamic environment, and, more particularly to devices for sealing an opening formed through biological tissue (such as blood vessels) made from such specially designed magnesium-aluminum alloys.

2. Description of the Related Art

Certain Mg alloys are known and have been used to form devices for sealing an opening formed through biological tissue (such as blood vessels). See, e.g., U.S. Pat. Pub. No. 20110046665, paras. [0015], [0018], [0025], and [0038] (describing a closure device for sealing an opening formed through biological tissue which comprises a footplate, a plug, and a wire, and where the footplate, wire, and/or plug portion is made from a biocompatible and biocorrodible metal comprising certain magnesium alloys).

Aluminum additions to Mg have a significant effect on corrosion rate, though a variety of trends can be found. Pardo reports that a 3% Al addition in Mg alloy AZ31 slightly decreases corrosion rate in 3.5% NaCl solution and that Al addition s of 8 to 9 wt. % found in AM80 and AZ91 strongly reduce corrosion rate in electrochemical testing in 3.5% NaCl solution (See A. Pardo, M. C. Merino, A. E. Coy, F. Viejo, R. Arrabal, S. Feliu, Jr., Electrochim. Acta, 53, 7890-7902 (2008)). Abady and co-workers found in electrochemical studies of alloys from 0 to 15 wt. % Mg exposed to chloride-free buffer solutions that corrosion rate peaked at 5 wt. % Al and decreased significantly in alloys with 10 and 15% Al (See G. M. Abady, N. H. Hilal, M. El-Rabiee, W. A. Badawy, Electrochim. Acta, 55, 6651-6658 (2010)). Kita et al. found from electrochemical testing that corrosion rate increases in dilute chloride environments with increasing Al content over the range of 1 to 9 mass percent (See H. Kita, M. Kimoto, T Kudo, J. Japan Inst. Of Metals, 69, 805-809 (2005)).

In simulated biological environments, the corrosion rate dependence appears to indicate that increasing Al content decreases rate. From electrochemical corrosion rate determinations of Mg-xAl-3Zn alloys exposed to quiescent modified simulated body fluid (SBF) at 36.5° C., corrosion rates were found to decrease strongly with increasing Al content (See Z. Wen, C. Wu, C. Dai, F. Yang, J. Alloys and Compounds, 488, 392-399 (2009)). Kirkland reported corrosion rates in Minimal Essential Medium (MEM) at 37° C. showing strongly decreased corrosion rate with increasing Al concentration over the range of 0 to 9 weight percent (See N. T. Kirkland, J. Lespagnol, N. Birbilis, M. P. Staiger, Corrosion Sci., 52, 287-291 (2010)).

Description of the Related Art Section Disclaimer: To the extent that specific patents/publications are discussed above in this Description of the Related Art Section or elsewhere in this Application, these discussions should not be taken as an admission that the discussed patents/publications are prior art for patent law purposes. For example, some or all of the discussed patents/publications may not be sufficiently early in time, may not reflect subject matter developed early enough in time and/or may not be sufficiently enabling so as to amount to prior art for patent law purposes. To the extent that specific patents/publications are discussed above in this Description of the Related Art Section and/or throughout the application, they are all hereby incorporated by reference into this document in their respective entirety(ies).

SUMMARY OF THE INVENTION

Figure 1:
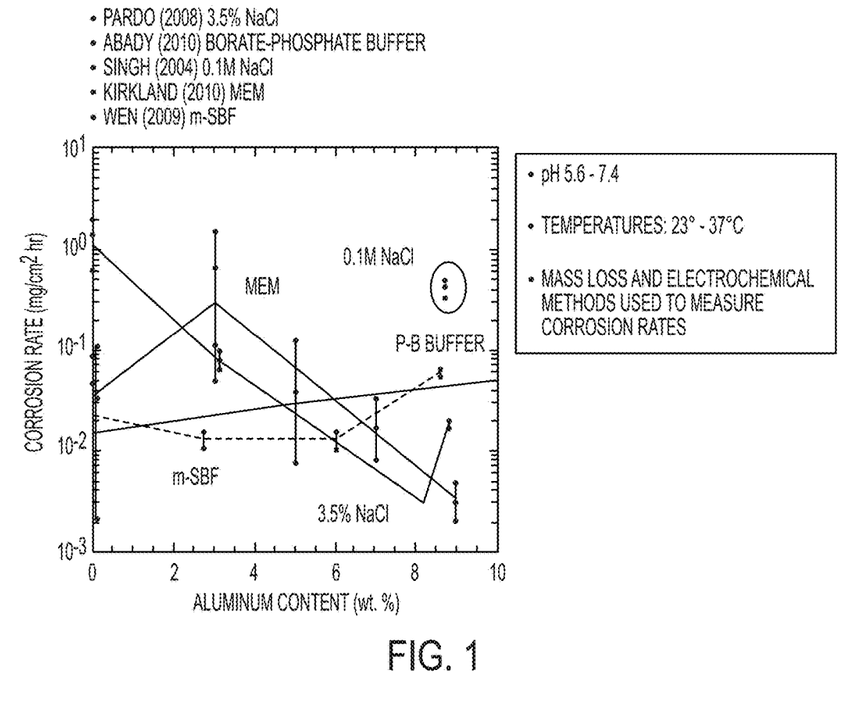
FIG. 1 is a graphical illustration showing that Mg corrosion rates in biological-stimulated environments have been shown to be affected by Al additions, albeit with apparent disparate results.

The present invention recognizes that there are potential problems and/or disadvantages with the conventional Mg—Al alloys and the unhelpful disparate results from the studies performed regarding these alloys referenced in the Description of the Related Art Section above. See FIG. 1 (The Singh reference cited in this figure and other figures is R. K. Singh Raman, N. Birbilis, J. Efthimiadis, Corrosion Engineering Science and Technology, Vol. 39, no. 4, p. 346 (2004); the remainder of the cited references in this figure and other figures herein are already referenced in this application). The apparently disparate findings is that the corrosion rate of Mg—Al alloys likely depends not just on the Al content, but on other factors such as the presence of other alloying elements, and the alloy microstructure. It is also likely to depend on the environment composition, pH, temperature, and in this particular case, flow rate of the contacting liquid medium. There is a need to determine whether SBF and MEM environments adequately mimic the mechanically dynamic physiological environment inside blood vessels. There is also a need to develop Mg—Al alloys that can be tuned to corrode at a particular predictable rate in a hemodynamic environment to suit the purpose of a particular closure device application. Various embodiments of the present invention may be advantageous in that they may solve or reduce one or more of the potential problems and/or disadvantages discussed above in this paragraph.

It is therefore a principal object and advantage of the present invention to provide specially designed Mg—Al alloys and medical uses thereof in a hemodynamic environment that overcome the problems and disparate findings of the prior art.

In accordance with the foregoing object and advantage, an embodiment of the present invention provides medical devices including closure devices made from such specially designed Mg—Al alloys. The closure device, or closure device implant, for sealing an opening formed through biological tissue can comprise a portion that sits in (or is at least partially exposed to) the lumen of a blood vessel (such as the femoral artery) ("footplate" portion), a portion that plugs the opening and may also be partially be exposed to the lumen of the blood vessel ("plug" portion), and portion that connects the footplate to the plug and may also be at least partially exposed to the lumen of the blood vessel ("wire" portion). It is contemplated that a closure device made from the Mg—Al alloys of the embodiments of the present invention may not contain each and every one of these specific portions. For example, the closure device may include only a wire portion and a plug portion, only a footplate portion and a plug portion, only a footplate portion and a wire portion, or only a footplate portion.

In accordance with an embodiment of the present invention, the specially designed Mg—Al alloys can include Mg—Al alloy compositions comprising Al alloy contents in any range that may result from the "tuning" for a particular purpose of the Mg—Al alloy (preferably within the range of 1 to 10% for the purposes disclosed herein). An amount of Fe can also be added to the Mg—Al alloy composition as a corrosion activator.

In accordance with an embodiment of the present invention, the ability to tune the in vivo corrosion rate of the closure device portion made from a Mg—Al alloy of an embodiment of the present invention by adjusting the Al alloy content of the Mg—Al alloy is provided.

In accordance with an embodiment of the present invention, at least one portion of the closure device can be made from a Mg—Al alloy of an embodiment of the present invention. Not all of the portions of the closure device need to be made from a Mg—Al alloy of an embodiment of the present invention. At least two of the portions of the closure device can be made from the same Mg—Al alloy of an embodiment of the present invention. Alternatively, in order to tune the corrosion rates of the particular portions of the closure device, the portions of the closure device can be made from different Mg—Al alloys of an embodiment of the present invention. For example, in order to tune the footplate to corrode at a greater rate than the plug, the footplate can be made from a Mg—Al alloy with a greater Al content percentage than the plug. Also, as understood by those skilled in the art, metallic corrosion is a surface phenomenon. By adjusting the surface area-to-volume ratio of the various closure device portions/components, the overall time for complete portion/component corrosion can be varied, or "tuned", to accommodate different residence times. While the corrosion rate of the material remains consistent (where, for example, the components are made from the same alloy), the topography of the individual components may be varied to provide greater or lesser surface area at which corrosion may occur, therefore providing faster overall component corrosion (and therefore shorter residence time in vivo) or slower overall component corrosion (and therefore longer relative residence time in vivo), respectively. In a preferable embodiment, the footplate is designed to have a greater surface area to volume ratio than the plug, thus resulting in a shorter residence time in vivo as compared to the plug.

As discussed more fully in the Detailed Description section below, the corrosion rate and biocompatibility of specially designed magnesium alloys with Al contents ranging from 1 to 8.25 wt. % were assessed using in vivo exposure to support the development of a novel percutaneous vascular closure device implants. The closure device implant is intended to stop bleeding in wounds associated with arteriotomies rapidly and completely by deploying a small implantable closure device implant delivered using a specially designed tool inserted into the wound. In this application, it is intended that the closure device implant be gradually absorbed over hours and days as natural healing takes place. This performance objective requires that a balance be struck between material corrosion rate (which is high in the overall context of bioimplanted metals), and wound healing rate. This contrasts the high corrosion resistance design objective, which is more common for implant materials.

BRIEF DESCRIPTION OF THE DRAWINGS

The present invention will be more fully understood and appreciated by reading the following Detailed Description in conjunction with the accompanying drawings, in which.

DETAILED DESCRIPTION

Reference will now be made in detail to the present preferred embodiments of the invention, examples of which are illustrated in the accompanying drawings.

In accordance with an embodiment of the present invention, closure device implants, such as the closure device implant shown and described in U.S. Pat. Pub. No. 20110046665 (which is incorporated by referenced herein in its entirety), can be made from the specially designed Mg—Al alloys of embodiments of the present invention. An embodiment of the closure device implant of U.S. Pat. Pub. No. 20110046665 is shown therein in its completely deployed configuration and position in FIG. 42. The closure device implant as shown in FIG. 42 of U.S. Pat. Pub. No. 20110046665 includes a footplate 110', a plug 111, and a wire 120. FIG. 42 also shows subcutaneous tissue 409 overlying a blood vessel 400, outside surface 402 and an inside surface 403 of a blood vessel wall 401 of the blood vessel 400. The closure device implant is shown sealing the opening/arteriotomy 405. Many other embodiments of the closure device implant, and of the closure device deployment device (see e.g., reference numeral 200, FIG. 53(a)), are shown and described in U.S. Pat. Pub. No. 20110046665 and are a part of certain embodiments of the present invention.

Figure 2:
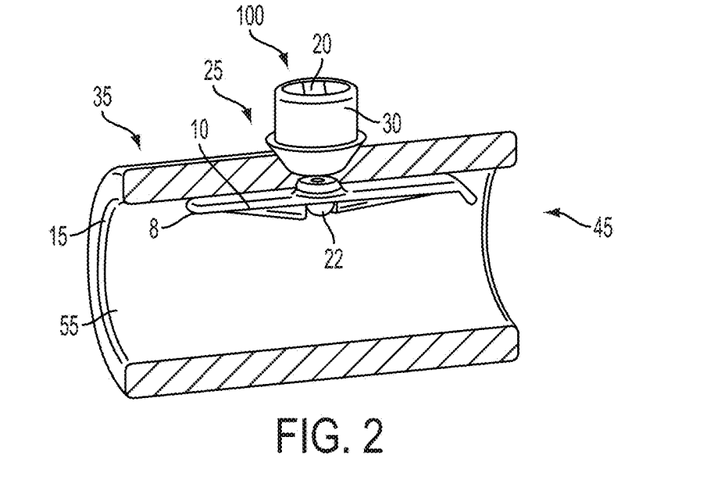
FIG. 2 is a perspective view of a closure device embodiment in a post-deployed arteriotomy sealing position and configuration that can be made from the specially designed Mg—Al alloys of embodiments of the present invention.

Another embodiment of the closure device implant can be made from the specially designed Mg—Al alloys of embodiments of the present invention includes the closure device implant 100 shown in FIG. 2. FIG. 2 shows a closure device implant including one or more of the following components—a footplate 10 which is seated on the inside surface 5 of the blood vessel wall 15 of a blood vessel 45 (blood vessel 45 is shown sectioned along its longitudinal axis in order to show the lumen 55), a plug 30 sealingly positioned within the arteriotomy 25, and a wire 20 connecting the footplate 10 with the plug 30, the wire 20 including a ball and socket connection at its distal end with the footplate and a plastically deformed bed at its proximal end securing the plug with the footplate. FIG. 2 illustrates the clamping of the arteriotomy 25 between the plug 30 and the footplate 10, preferably giving a stable construct and immediate hemostasis, according to an embodiment of the present invention.

It is contemplated that other existing (or as yet to exist) closure device-type implants can be made from the specially designed Mg—Al alloys of embodiments of the present invention. If a portion of a device that is used to seal an opening formed through a blood vessel is exposed to blood in the lumen of a blood vessel and biocompatibility and a particular corrosion rate is desired, the device can be made from the specially designed Mg—Al alloys of embodiments of the present invention. Such devices are shown and described in, for example, U.S. Pat. Nos. 4,744,364, 5,222,974, 5,282,827, 5,441,517, 5,676,689, 5,861,004, 6,045,569, 6,007,563, 6,090,130, 5,545,178, 5,531,759, 5,593,422, 5,916,236, 6,890,343, and 6,969,397, all of which are hereby incorporated by reference herein in their respective entirety(ies).

Advantages of the invention are illustrated by the Examples Section, below. However, the particular materials and amounts thereof recited in these examples, as well as other conditions and details, are to be interpreted to apply broadly in the art and should not be construed to unduly restrict or limit the invention in any way.

The Examples Section describes the in vivo evaluation of the corrosion rate, corrosion mode and biocompatibility of Mg—Al alloys in a hemodynamic environment. An objective of the described studies is to select an Mg—Al alloy for a closure device implant that is entirely biocompatible and rapidly bioabsorbable. Short terms goals include the creation of a closure device implant that facilitates immediate hemostasis upon deployment, causes a minimal, if any, acute inflammatory response, avoidance of embolisms, and allows for accelerated patient ambulation. Long term goals include rapid and complete bioabsorption of at least the intraluminal footplate component (approx. 1-2 days), wound healing, no loss of vessel patency, and no deleterious systemic effects from chemical exposure (e.g., corrosion byproducts, hydrogen evolution).

EXAMPLES

Example 1

AZ31 Implant Material

This Example describes the implanting of a footplate made from AZ31 in a sheep aorta, in order to study the corrosive effects of this hemodynamic environment on such a magnesium alloy.

Figure 3A:
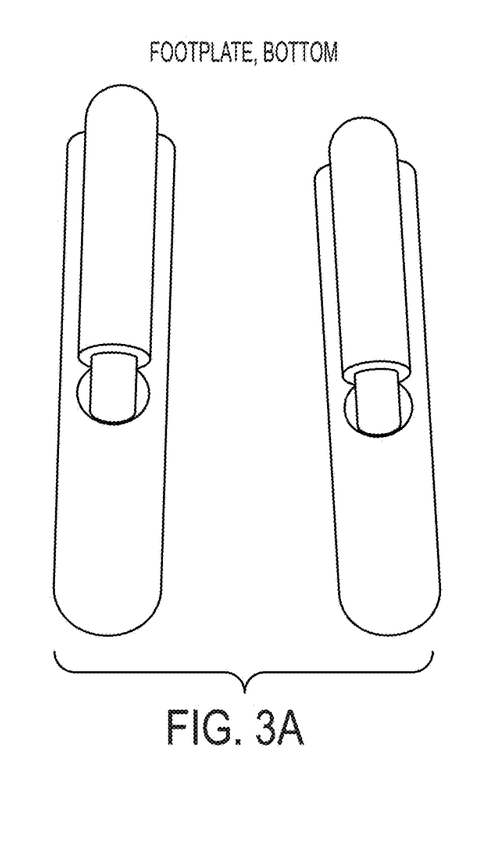
FIG. 3(a)-(b) show pictures of the results of a 15-day explant, sheep aorta (retroperitoneal approach) vs. an uncorroded specimen.
Figure 3B:
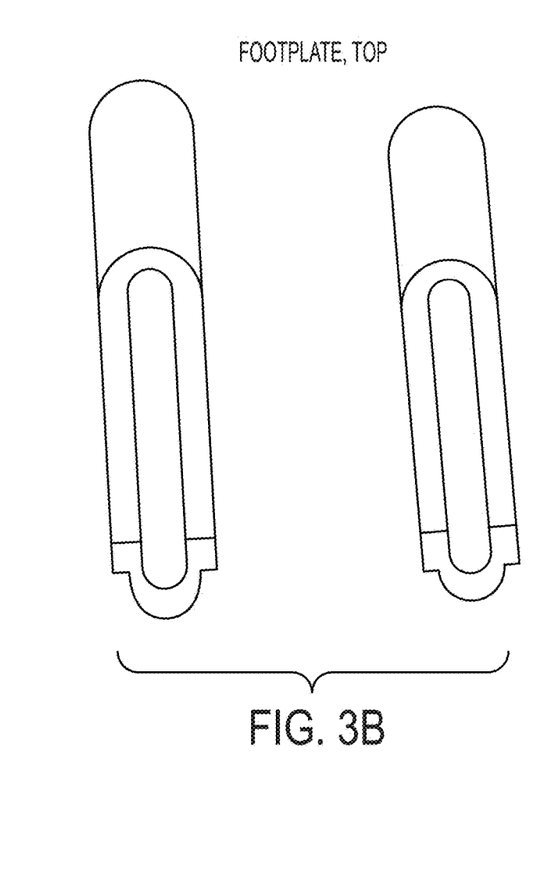

FIG. 3(a)-(b) show pictures of the results of a 15-day explant, sheep aorta (retroperitoneal approach) vs. an uncorroded specimen. FIG. 3(a) shows the bottoms of the respective footplates, and FIG. 3(b) shows the tops of the respective footplates, where the uncorroded footplate specimen is positioned on the left hand side in each of FIGS. 3(a) and 3(b). It is estimated that the time to complete absorption would be approximately 150 days.

An aim of the following Example is to characterize the effect of Al content on the alloy dissolution rate in a physiological hemodynamic environment. The biocompatibility of Mg is known, but a more rapid bioabsorption rate is an objective for the closure device implant embodiments.

Example 2

This Example describes an in vivo study undertaken to determine bioabsorption kinetics by corrosion of certain Mg—Al alloys. The study was performed in vivo in sheep femoral arteries; an analog to the human femoral model as it has similar blood flow conditions, similar blood chemistry, similar lumen and arterial wall physiology, and similar endothelial physiology. Also, the pathological tissue reaction to the implants is similar to that in humans. The animals used in this study (animal G3924—sacrificed at 8 hrs.; animal G3918—sacrificed at 4 hours) were 2+ years old, and 200+ lbs.

In brief, small cylindrical Mg alloys samples measuring 0.74 mm in diameter and 5.1 mm in length were implanted in the femoral arteries of sheep (cut-down procedure) using an 18-gauge access needle, and secured to the vessel wall by a single suture. In this way, samples were exposed to environmental effects associated with live blood flow and chemistry, vessel contraction, vessel wall texture, and endothelia growth in a manner consistent with the operation of the vascular closure device.

Five different alloys were studied. The Mg alloy samples included AZ31 as a commercial alloy control. The remaining alloys possessed Mg—Al—Fe ternary compositions. Alloy chemistry and surface preparation were used to modulate corrosion rates. Transition metals including the Al alloy contents ranged from 1 to 8.25 wt. %, as shown in Table 1 below. A small amount of Fe was added to the alloys as a corrosion activator. Transition metals including Fe are strong corrosion activators of Mg corrosion. Al and Zn additions allow mechanical properties to be varied. Al and Zn additions to Mg do not significantly affect corrosion rate of Mg in dilute chloride solutions. See Joseph R. Davis, Metals Handbook, FIG. 1 (showing a graphical illustration of the effect of alloying and contaminant metals on the corrosion rate of magnesium as determined by alternate immersion in 3% NaCl solution).

TABLE 1

Special Mg—Al—Fe Alloys Were Cast and Drawn for In Vivo Corrosion Rate Studies

| Alloy | Al (wt. %) | Fe (wt. %) |
| --- | --- | --- |
| 1. | 1.06 - Mg1Al or Mg1.06Al | <0.01 |
| 2. | 2.94 - Mg3Al or Mg2.94Al | 0.07 |
| 3. | 6.09 - Mg6Al or Mg6.09Al | 0.07 |
| 4. | 8.25 - Mg8Al or Mg8.25Al | 0.05 |
| AZ31 | 3.0 - | (1.0 Zn) |

The samples were then chemically treated in either a ferrous-sulfate-modified sulfuric acid or acetic acid solution.

Samples were treated, for example, in an aqueous solution of lg of 98% sulfuric acid $H_2SO_4$ and 0.04 g $FeSO_4$ in 10 mL of distilled water for 2 minutes to enrich the surface with Fe and transition metal impurities. This surface treatment was carried out in an attempt to further stimulate corrosion.

Figure 9:
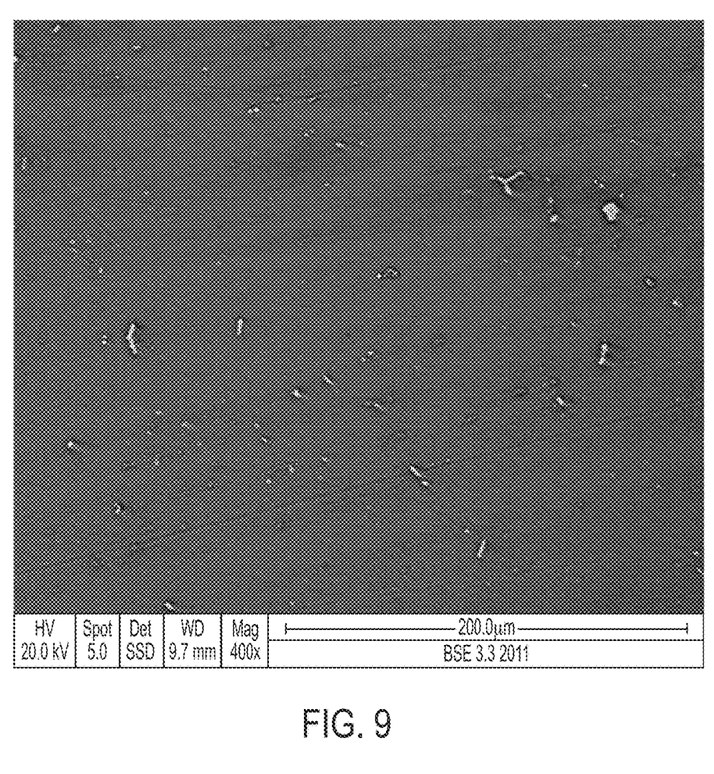
FIG. 9 is an SEM image showing transition metal-rich intermetallic particles (Al with Mg background and trace amounts of Fe) evenly dispersed through the constituent experimental alloys.

FIG. 9 is a scanning electron micrograph (SEM) image showing a polished cross section of the Mg—Al—Fe alloy, according to an embodiment of the present invention. Impurity elements and transition metals such as Fe and Mn (which may be impurities themselves) are concentrated in these particles. Particles of this type are important initiation sites for corrosion in Mg alloys and may be considered activating sites for corrosion. Having a dispersion of corrosion initiation sites is important for achieving a high corrosion rate and ensuring that the corrosion remains more or less uniform across the component surface. The transition metal-rich intermetallic particles shown have a basically consistent, even, and homogenous dispersion through the experimental alloys. This dispersion, as discussed in the results section below, results in a basically even corrosion rate—a uniform corrosion behavior.

Six implants were added per femoral artery; 1 cm apart (1 of each of 4 Mg—Al—Fe plus two AZ31 as controls).

Figure 4:
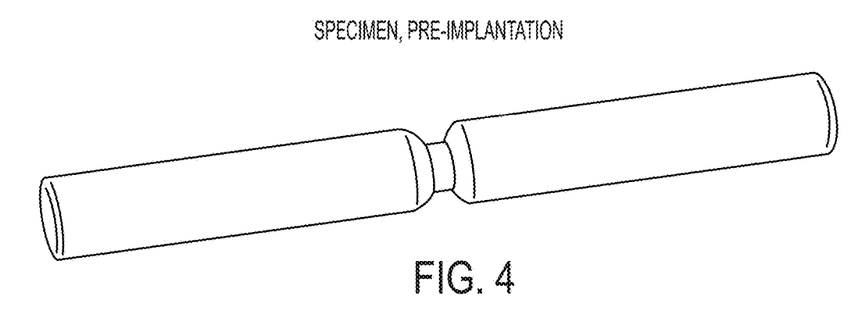
FIG. 4 shows a picture of one of the implant specimens prior to implantation into a sheep femoral artery, according to an embodiment of the present invention.

FIG. 4 shows a picture of one of the implant specimens prior to implantation into a sheep femoral artery, according to an embodiment of the present invention.

Figure 5:
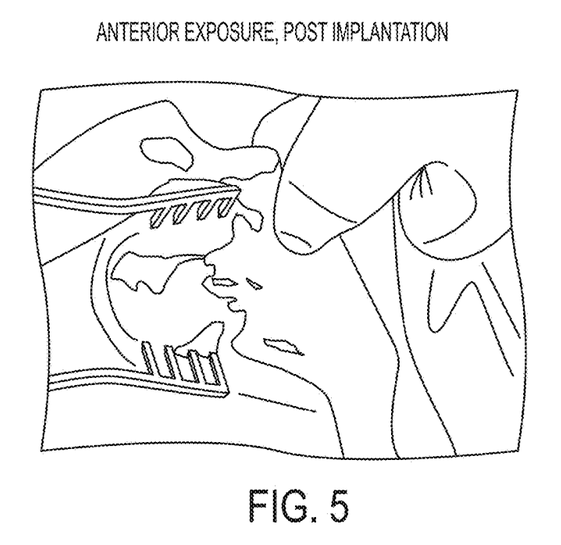
FIG. 5 shows a picture of the anterior exposure, post implantation into a sheep femoral artery, according to an embodiment of the present invention.
Figure 6A:
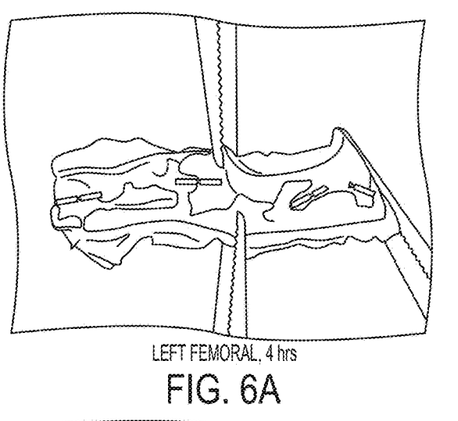
FIGS. 6(a)-(d) shows ex vivo gross histology of (a) the left femoral artery after 4 hours of implantation, (b) the left femoral artery after 8 hours of implantation, (c) the right femoral artery after 4 hours of implantation, and (d) the right femoral artery after 8 hours of implantation.
Figure 6B:
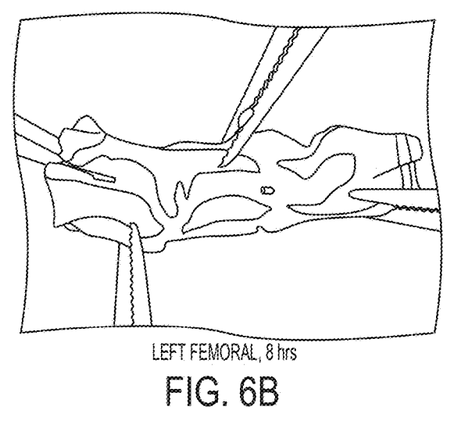
Figure 6C:
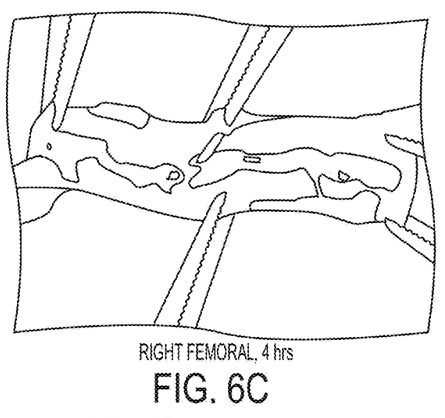
Figure 6D:
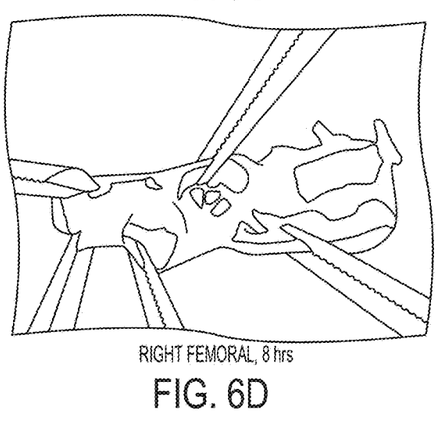
Figure 7A:
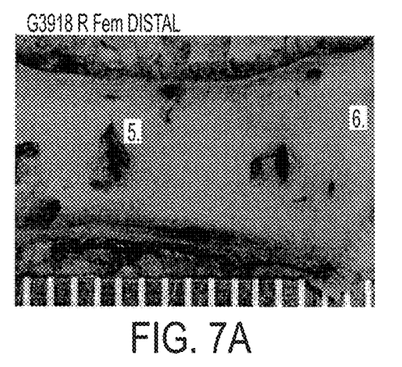
FIGS. 7(a)-(d) shows the histopathology of portions of the sheep (animal G3918) femoral arteries, showing little to no inflammatory reaction, according to an embodiment of the present invention.
Figure 7B:
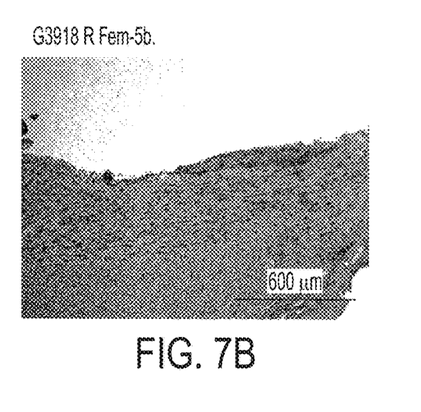
Figure 7C:
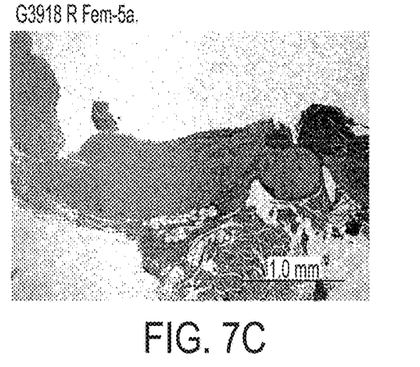
Figure 7D:
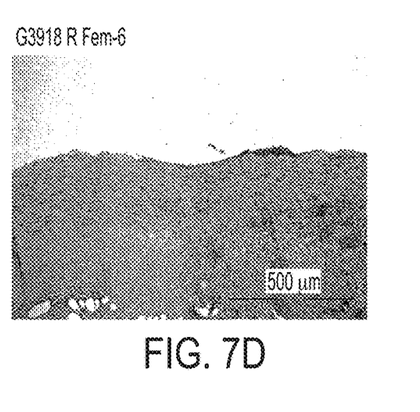

FIG. 5 shows a picture of the anterior exposure, post implantation into a sheep femoral artery, according to an embodiment of the present invention.

FIGS. 6(a)-(d) shows ex vivo gross histology of (a) the left femoral artery after 4 hours of implantation, (b) the left femoral artery after 8 hours of implantation, (c) the right femoral artery after 4 hours of implantation, and (d) the right femoral artery after 8 hours of implantation.

FIGS. 7(a)-(d) shows the histopathology of portions of the sheep (animal G3918) femoral arteries, showing little to no inflammatory reaction, according to an embodiment of the present invention.

Tables 2 and 3, below, show the weight loss analysis of the sheep implants made from the alloys set forth in Table 1.

TABLE 2

Animal G3924, Sacrificed at 8 hours

| Implant Position Proximal-to-Distal | Alloy | Right Femoral explant weight original weight (g) | % wt Lost | Left Femoral explant weight original weight (g) | % wt Lost |
|---|---|---|---|---|---|
| 3 | Mg6Al | .00141 .00358 | 61 | .00256 .00359 | 29 |
| 4 | Mg3Al | .00256 .00345 | 26 | .00288 .00340 | 15 |
| 5 | Mg1Al | .00331 .00338 | 2.0 | .00326 .00332 | 1.8 |
| 6 | Mg8Al | .00050 .00345 | 85.5 | .00191 .00341 | 44 |

TABLE 3

Animal G3918, Sacrificed at 4 hours

| Implant Position Proximal-to-Distal | Alloy | Right Femoral explant weight original weight (g) | % wt Lost | Left Femoral explant weight original weight (g) | % wt Lost |
|---|---|---|---|---|---|
| 1 | Mg6Al | .00288 .00357 | 19 | .00295 .00348 | 15 |
| 2 | Mg3Al | .00305 .00348 | 12 | .00304 .00342 | 11 |
| 3 | Mg1Al | .00328 .00333 | 1.5 | .00329 .00333 | 1.2 |
| 4 | Mg8Al | .00259 .00333 | 22 | .00263 .00337 | 22 |

The results show that all of the experimental Mg—Al alloys were completely dissolved within 5 days of exposure, indicating a corrosion rate that is dramatically faster than Mg alloy AZ31, which was scarcely attacked in short-duration exposures. Corrosion rates were found to increase with increasing Al content; a trend that is at odds with at least some of the corrosion rate data reported for Mg—Al alloys in SBF and MEM. In the study carried out by Wen et al., AZ91 was found to corrode at a rate of about 0.01 mg/cm2-hr (See Z. Wen, C. Wu, C. Dai, F. Yang, J. Alloys and Compounds, 488, 392-399 (2009)), while Kirkland et al. found a corrosion rate of 0.004 mg/cm2-hr for Mg-9Al (See N. T. Kirkland, J. Lespagnol, N. Birbilis, M. P. Staiger, Corrosion Sci., 52, 287-291 (2010)).

Figure 8:
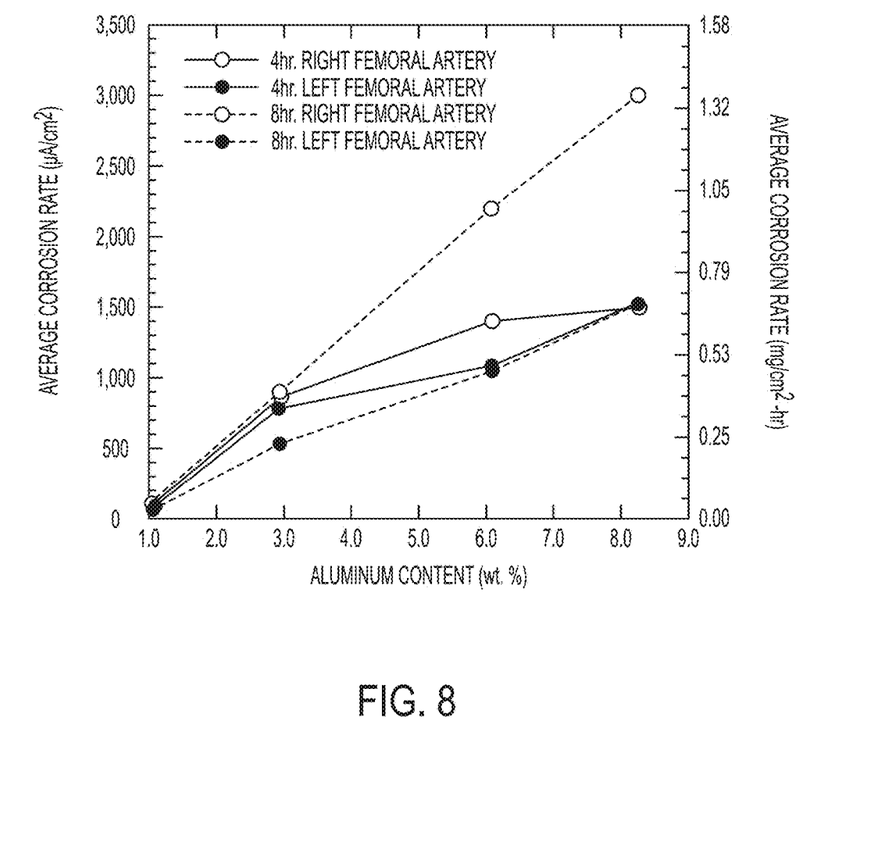
FIG. 8 is a graphical illustration showing the in vivo corrosion rate versus Al content for the Mg—Al—Fe alloys examined by mass loss, according to an embodiment of the present invention.

FIG. 8 shows that the corrosion rate for surface treated Mg-8.25Al exposed in vivo corrode at rates ranging from 0.6 to 1.3 mg/cm2-hr, which is about 2 orders of magnitude faster than in quiescent simulated in vitro environments. The results show a strong dependence of corrosion rate on Al content, and corrosion rates that are suitable for closure device implant applications.

Figure 10A:
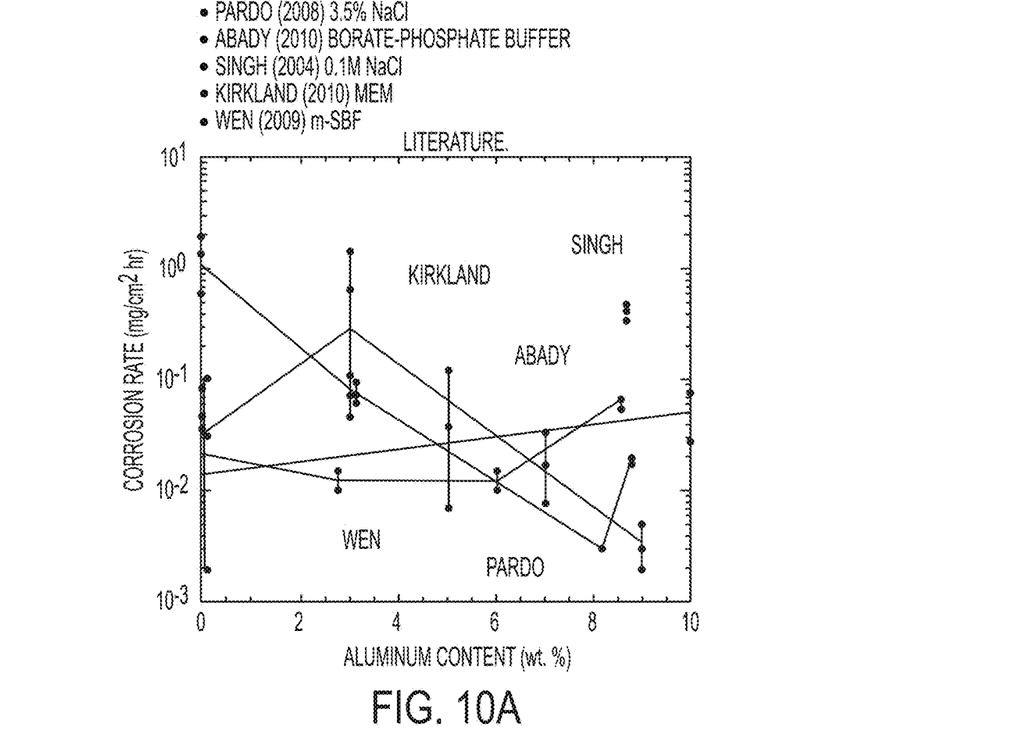
FIGS. 10(a)-(b) show a comparison of corrosion rates in bio-environment stimulants, in the existing literature vs. hemodynamic exposure, according to an embodiment of the present invention.
Figure 10B:
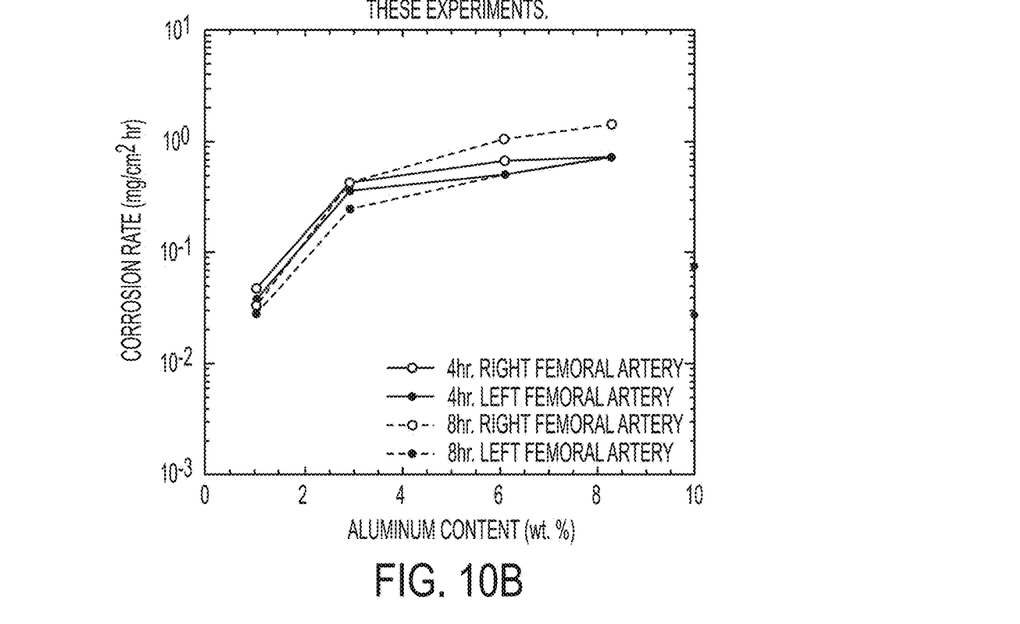

FIGS. 10(a)-(b) show a comparison of corrosion rates in bio-environment stimulants, as discussed in some of the referenced existing literature vs. hemodynamic exposure, according to an embodiment of the present invention.

Figure 11:
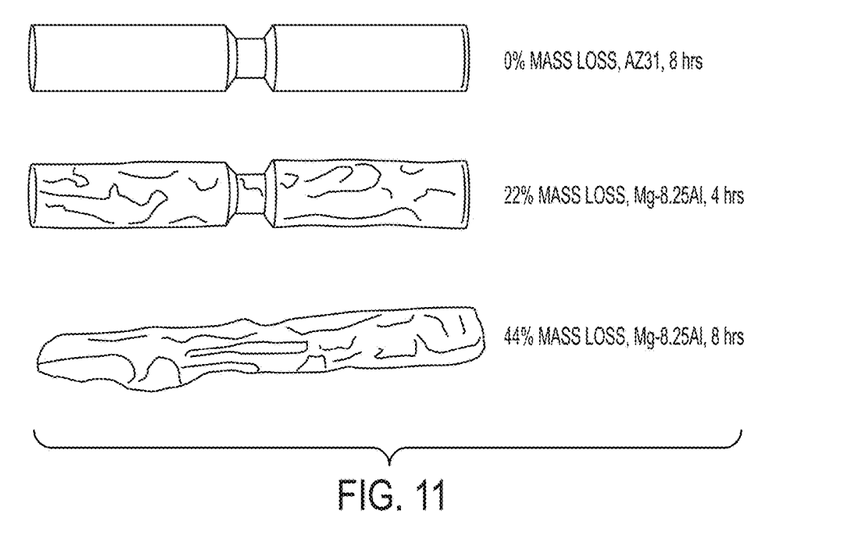
FIG. 11 is an optical micrograph of explanted Mg alloy samples showing the extent of corrosion, according to an embodiment of the present invention. AZ31 after 8 hours (is shown at the top), Mg-8.25Al after 4 hours exposure (is shown at the middle), and Mg-8.25Al after 8 hours exposure (is shown at the bottom).

In terms of corrosion morphology, the attack observed is essentially uniform in nature (uniform localized corrosion). Corrosion of the experimental Mg—Al—Fe alloys was rapid relative to AZ31. FIG. 11 is an optical micrograph of explanted Mg alloy samples showing the extent of corrosion. AZ31 after 8 hours (is shown at the top), Mg-8.25Al after 4 hours exposure (is shown at the middle), and Mg-8.25Al after 8 hours exposure (is shown at the bottom).

Dark corrosion product, which is presumably mixed Mg and Al hydroxide is evident in histological examination of explanted arterial segments. There is no indication of negative immune response; even in separate longer-term studies lasting tens of days. Indeed, separate studies of the closure device implant and its components show endothelialization of Mg alloy components and good wound closure and healing.

These results indicate that the specially designed Mg—Al alloys demonstrate corrosion rates in a hemodynamic environment that will result in bioabsorption of the Mg based components of embodiments of the closure device implant in timeframes (preferably approx. 1-2 days, and up to five days) that are appropriate for the application. The results also suggest the ability to tune the in vivo corrosion rate significantly by adjusting the Al alloy content of Mg—Al—Fe alloys. This tuning can be done depending upon need.

Example 3

Surface Pretreatment of Magnesium and Magnesium Alloys for Tailoring Corrosion Rate This Example describes the modification of magnesium and magnesium alloy surfaces to increase, temporarily or permanently, the dissolution rate for in vivo environments.

In brief, the process involves contacting the alloy with a specially prepared aqueous solution by dipping, spraying or brushing followed by rinsing and drying in clean water. The solution composition is defined by the addition of a suitable acid to activate the alloy and modify the pH of the solution, and an accelerant, which is specifically selected to achieve increased corrosion. Through this process, the surface composition of the alloy is modified by (1) enriching it in impurities already contained in the alloy as the Mg component corrodes preferentially, and (2) depositing product(s) from solution that are associated with the acid and accelerant addition.

Suitable inorganic acids include sulfuric, nitric, hydrochloric and phosphoric and phosphonic. Acid concentrations may range from 1 mg to 10 g per liter of solution. Suitable organic acids include citric, tartaric, acetic and oxalic. Suitable accelerants are generally soluble transition metal salts, typically though not exclusively of iron, manganese, and cobalt. Accelerant concentrations are typically much less than acid concentrations and range from 0.01 mg to 1 g per liter of solution.

The contact time between solution and treated surface may be varied to further adjust corrosion rate. Contact times may range from 5 seconds to 10 minutes based on the chemistry of the pretreatment solution and the desired corrosion rate. After pretreatment, surfaces are rinsed thoroughly with distilled or deionized water to halt the interaction between the pretreatment solution and the alloy. No further treatment of the surface is needed prior to use. The following is an example of the process.

Mg alloys samples were pretreated by immersion in an aqueous solution of 1 g of 98% sulfuric acid $H_2SO_4$ and 0.04 g of ferrous sulfate $FeSO_4$ in 10 mL of distilled water. Samples were treated in batches of 25 by alloy type for a minimum of 90 seconds and no longer than 120 seconds. Samples were rinsed and dried in air after immersion in the pretreatment solution. Sample batches were weighed before and after pretreatment. Mass losses were calculated and per sample mass losses were estimated as shown in the following Table 4.

TABLE 4

|        | Initial | Final | Chang Initial per sample | Change per sample | Pct. |
|--------|---------|-------|--------------------------|-------------------|------|
| AZ 31B | 96.4    | 90.3  | 6.1                      | 3.9               | 0.24 | 6.3% |
| Mg-1Al | 91.7    | 84.8  | 6.9                      | 3.7               | 0.28 | 7.5% |
| Mg-3Al | 89.4    | 85.8  | 3.6                      | 3.6               | 0.14 | 4.0% |
| Mg-5Al | 84.5    | 75.7  | 8.8                      | 3.4               | 0.35 | 10.4% |
| Mg-8Al | 88.3    | 76.8  | 11.5                     | 3.5               | 0.46 | 13.0% |

The results show that mass loss increases regularly for the Mg-3Al, Mg-6Al and Mg-8Al samples from 0.14 to 0.46 mg per sample. This response is consistent with the expectation that Mg—Al alloy dissolution rate increases with increasing Al content. The mass losses for AZ31 and Mg-1Al samples were 0.24 and 0.28 mg per sample and appear out of the trend presented by the other samples. These two batches of samples were exposed to the pretreatment solution for times longer than 90 seconds due to difficulty in removing and washing the very small samples. The pretreatment protocol was refined for the Mg-3Al, Mg-6Al and Mg-8Al samples and their immersion times were very close to the 90 second target. All of the samples except the AZ31B samples presented bright lustrous surfaces after pretreatment. The AZ31 B samples were slightly darkened.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A closure device implant for sealing an opening formed through a blood vessel, said closure device comprising:
    a plug comprising a proximal end and a distal end;
    a wire extending from a position distal to said plug's distal end through said plug; and
    a footplate attached to said wire and positioned distally to said distal end of said plug;
    wherein at least one of said wire, said plug, and said footplate is formed of a biocorrodible metal comprising a magnesium alloy formulated with a corrosion activator comprising between 0.01% and 0.08% iron, wherein said footplate portion's magnesium alloy comprises between about 1% to 8.25% aluminum, wherein said magnesium alloy formulated with the corrosion activator is formulated to have a faster corrosion rate in a hemodynamic environment than a corrosion rate of AZ31.

2. The closure device implant of claim 1, wherein said magnesium alloy comprises between 3% and 8.25% aluminum.

3. The closure device implant of claim 2, wherein said magnesium alloy further comprises between 0.01% and 0.05% iron.

4. The closure device implant of claim 2, wherein each of said footplate, said wire, and said plug comprise about the same percentages of aluminum.

5. The closure device implant of claim 2, wherein each of said footplate, said wire, and said plug comprise different percentages of aluminum.

6. The closure device of claim 5, wherein said footplate comprises a greater percentage of aluminum as compared with said plug.

7. The closure device of claim 5, wherein said footplate comprises a lower percentage of aluminum as compared with said plug.

8. The closure device of claim 5, wherein said footplate comprises a greater percentage of aluminum as compared with said wire.

9. The closure device of claim 5, wherein said footplate comprises a lower percentage of aluminum as compared with said wire.

10. The closure device of claim 5, wherein said plug comprises a greater percentage of aluminum as compared with said wire.

11. The closure device of claim 5, wherein said plug comprises a lower percentage of aluminum as compared with said wire.

12. The closure device implant of claim 2, wherein each of said footplate, said wire, and said plug comprise different surface area to volume ratios.

13. The closure device of claim 1, wherein the surface area to volume ratio of each of the footplate, wire, and plug is about the same.

14. The closure device of claim 1, wherein the surface area to volume ratio of the footplate is greater than the surface area to volume ratio of the plug.

15. The closure device of claim 1, wherein the surface area to volume ratio of the footplate is less than the surface area to volume ratio of the plug.

16. The closure device of claim 1, wherein the surface area to volume ratio of the footplate is greater than the surface area to volume ratio of the wire.

17. The closure device of claim 1, wherein the surface area to volume ratio of the footplate is less than the surface area to volume ratio of the wire.

18. The closure device of claim 1, wherein the surface area to volume ratio of the plug is greater than the surface area to volume ratio of the wire.

19. The closure device of claim 1, wherein the surface area to volume ratio of the plug is less than the surface area to volume ratio of the wire.

\* \* \* \* \*

UNITED STATES PATENT AND TRADEMARK OFFICE
CERTIFICATE OF CORRECTION

PATENT NO. : 9,931,441 B2  
APPLICATION NO. : 14/879275  
DATED : April 3, 2018  
INVENTOR(S) : Stephen Green et al.

Page 1 of 1

It is certified that error appears in the above-identified patent and that said Letters Patent is hereby corrected as shown below:

In the Claims

Column 10, Line 47, please insert --implant-- between "device" and "of"
Column 10, Line 50, please insert --implant-- between "device" and "of"
Column 10, Line 53, please insert --implant-- between "device" and "of"
Column 10, Line 56, please insert --implant-- between "device" and "of"
Column 10, Line 59, please insert --implant-- between "device" and "of"
Column 10, Line 62, please insert --implant-- between "device" and "of"
Column 11, Line 1, please insert --implant-- between "device" and "of"
Column 11, Line 4, please insert --implant-- between "device" and "of"
Column 11, Line 7, please insert --implant-- between "device" and "of"
Column 11, Line 10, please insert --implant-- between "device" and "of"
Column 11, Line 13, please insert --implant-- between "device" and "of"
Column 11, Line 16, please insert --implant-- between "device" and "of"
Column 11, Line 19, please insert --implant-- between "device" and "of"

Signed and Sealed this  
Thirteenth Day of November, 2018

Andrei Iancu  
*Director of the United States Patent and Trademark Office*